(12) United States Patent
Bjornson et al.

(10) Patent No.: US 7,811,523 B2
(45) Date of Patent: Oct. 12, 2010

(54) MICROFLUIDIC ANALYTICAL APPARATUS

(75) Inventors: Torleif Bjornson, Gilroy, CA (US);
Kevin Maher, Woodside, CA (US)

(73) Assignee: Monogram Biosciences, South San Francisco, CA (US)

( * ) Notice: Subject to any disclaimer, the term of this patent is extended or adjusted under 35 U.S.C. 154(b) by 436 days.

(21) Appl. No.: 11/761,350

(22) Filed: Jun. 11, 2007

(65) Prior Publication Data

US 2007/0264160 A1 Nov. 15, 2007

Related U.S. Application Data

(62) Division of application No. 10/496,684, filed as application No. PCT/US02/41651 on Dec. 6, 2002, now abandoned.

(60) Provisional application No. 60/341,664, filed on Dec. 17, 2001.

(51) Int. Cl.
*B01D 57/02* (2006.01)
(52) U.S. Cl. .................. 422/104; 204/601; 204/451
(58) Field of Classification Search ............. 359/333; 204/604, 450, 451, 453, 422, 99; 422/99
See application file for complete search history.

(56) References Cited

U.S. PATENT DOCUMENTS

| | | | |
|---|---|---|---|
| 4,455,758 A * | 6/1984 | Iwafune et al. ................. 33/282 |
| 4,760,335 A | 7/1988 | Linberg | |
| 5,061,989 A | 10/1991 | Yen | |
| 5,302,891 A | 4/1994 | Wood et al. | |
| 5,610,684 A * | 3/1997 | Shiraishi ...................... 355/55 |
| 5,896,037 A | 4/1999 | Kudla et al. | |
| 6,143,152 A | 11/2000 | Simpson et al. | |
| 6,271,480 B1 | 8/2001 | Yamaguti | |
| 6,375,871 B1 | 4/2002 | Bentsen | |
| 6,420,622 B1 | 7/2002 | Johnston | |
| 6,451,191 B1 | 9/2002 | Bentsen | |
| 6,827,831 B1 * | 12/2004 | Chow et al. .................. 204/604 |
| 7,102,992 B1 * | 9/2006 | Dalziel ....................... 369/300 |
| 2001/0020588 A1 * | 9/2001 | Adourian et al. ............ 204/451 |
| 2002/0098124 A1 | 7/2002 | Bentsen | |
| 2002/0195345 A1 | 12/2002 | Bentsen | |

FOREIGN PATENT DOCUMENTS

WO    WO 99/19717    4/1999

\* cited by examiner

*Primary Examiner*—Jill Warden
*Assistant Examiner*—Timothy G Kingan

(57) ABSTRACT

A microfluidic analytical apparatus (10) comprising a microfluidic card pairing (12) with a corresponding circuit card (14) and the circuit card pairing (12) with corresponding conductive fingers (16). The microfluidic card (12) has a plurality of channels (32) and ports (54) on a top surface of the card in a desired configuration, the ports (54) in fluid communication with the channels (32). The circuit card (14) has a plurality of conductive pins (60) projecting from a bottom surface of the card and having a configuration that corresponds to the particular configuration of the ports (54) of the microfluidic card (12) that is paired with. The circuit card (14) is received within a holder (20) that provides that provides multiple functions. Conductive pads (18) are disposed on a top surface of the circuit card (14), the pads (18) in electrical communication with the conductive pins (60) and corresponding to a configuration of conductive fingers (16) connected to a power source to provide voltage to the microfluidic card (12) for analytical operations. Additionally, detection difficulties associates with non-uniformities present on the card surface are overcome using a detection system incorporating a compliantly mounted microscopic head.

14 Claims, 6 Drawing Sheets

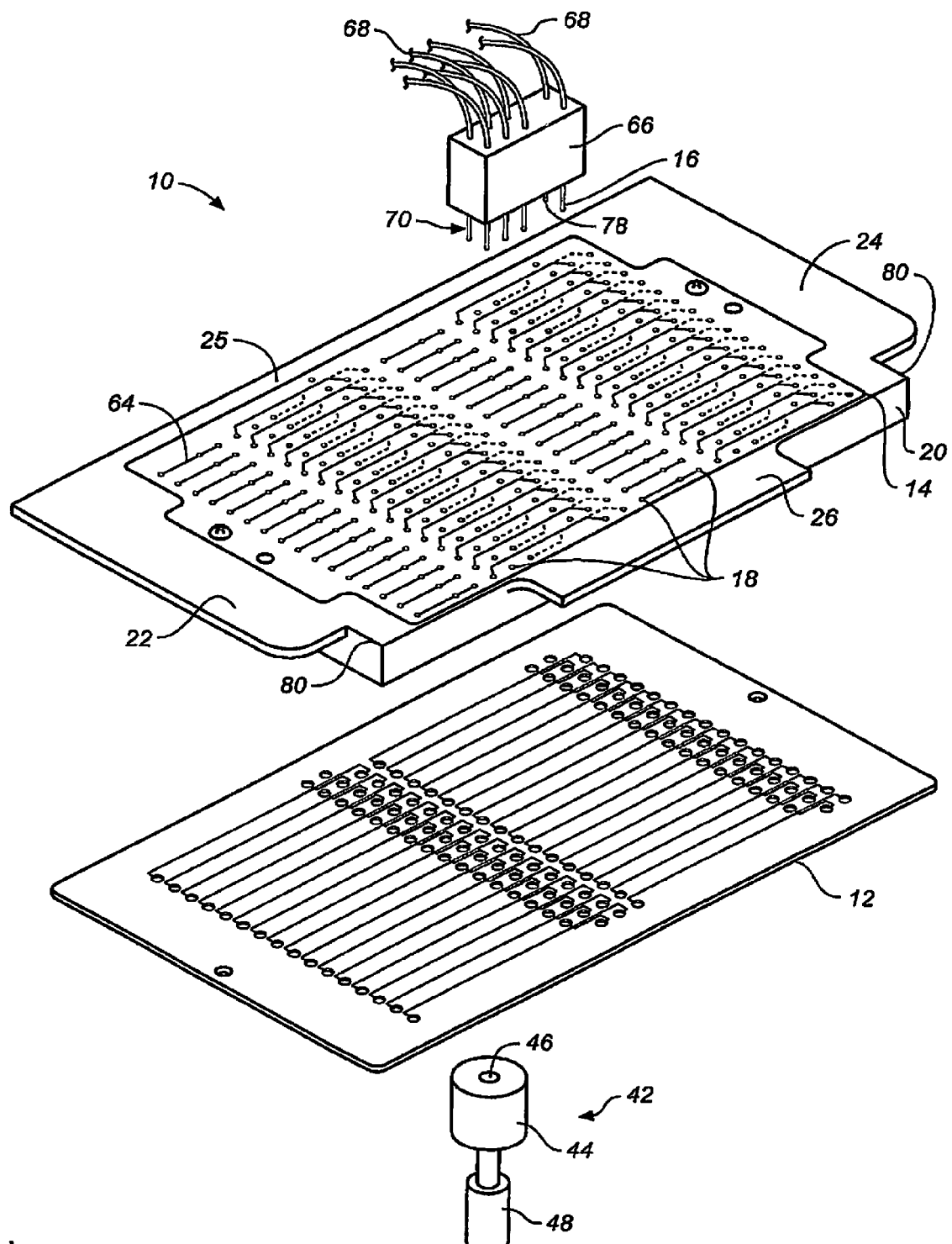
FIG._1

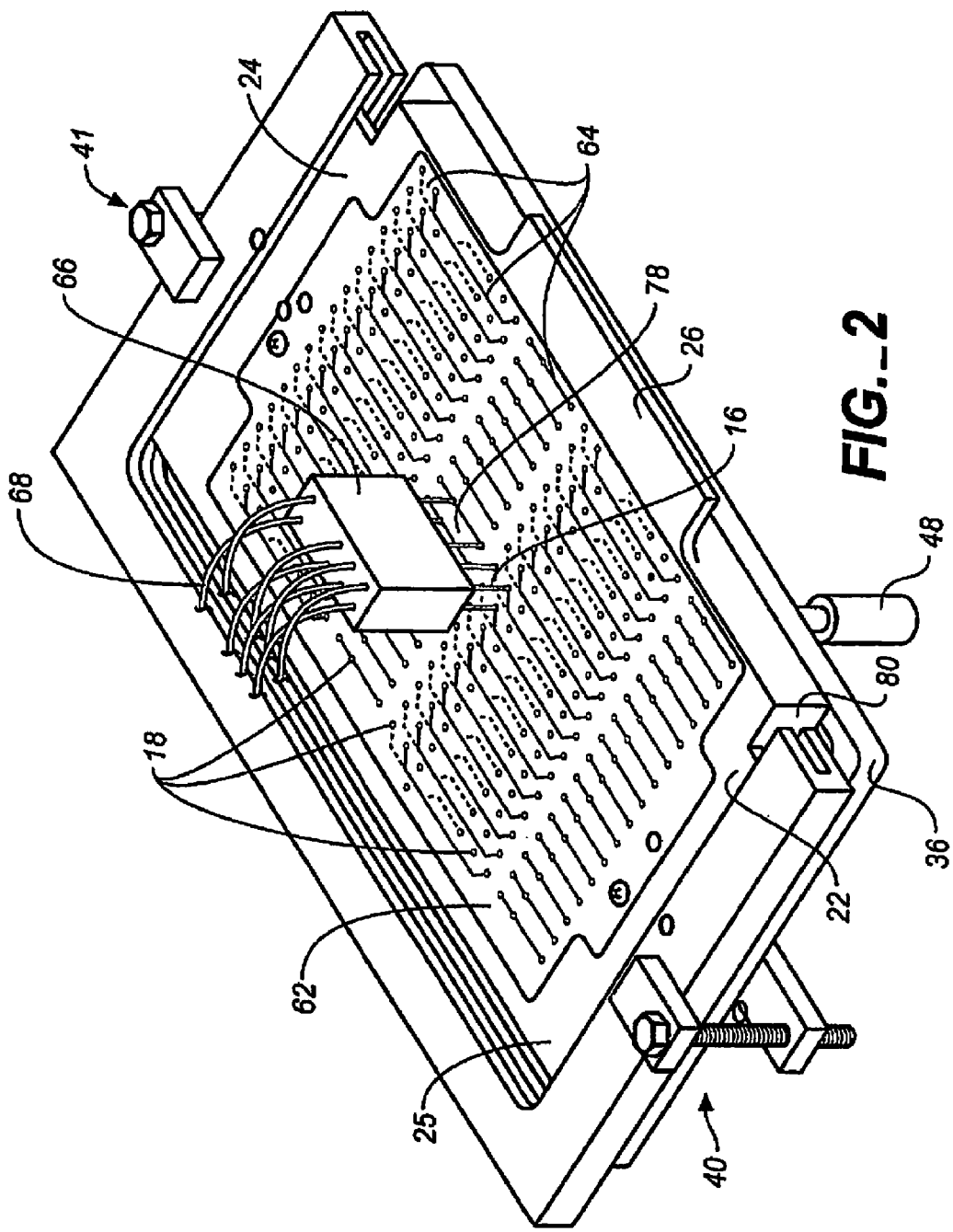
FIG._2

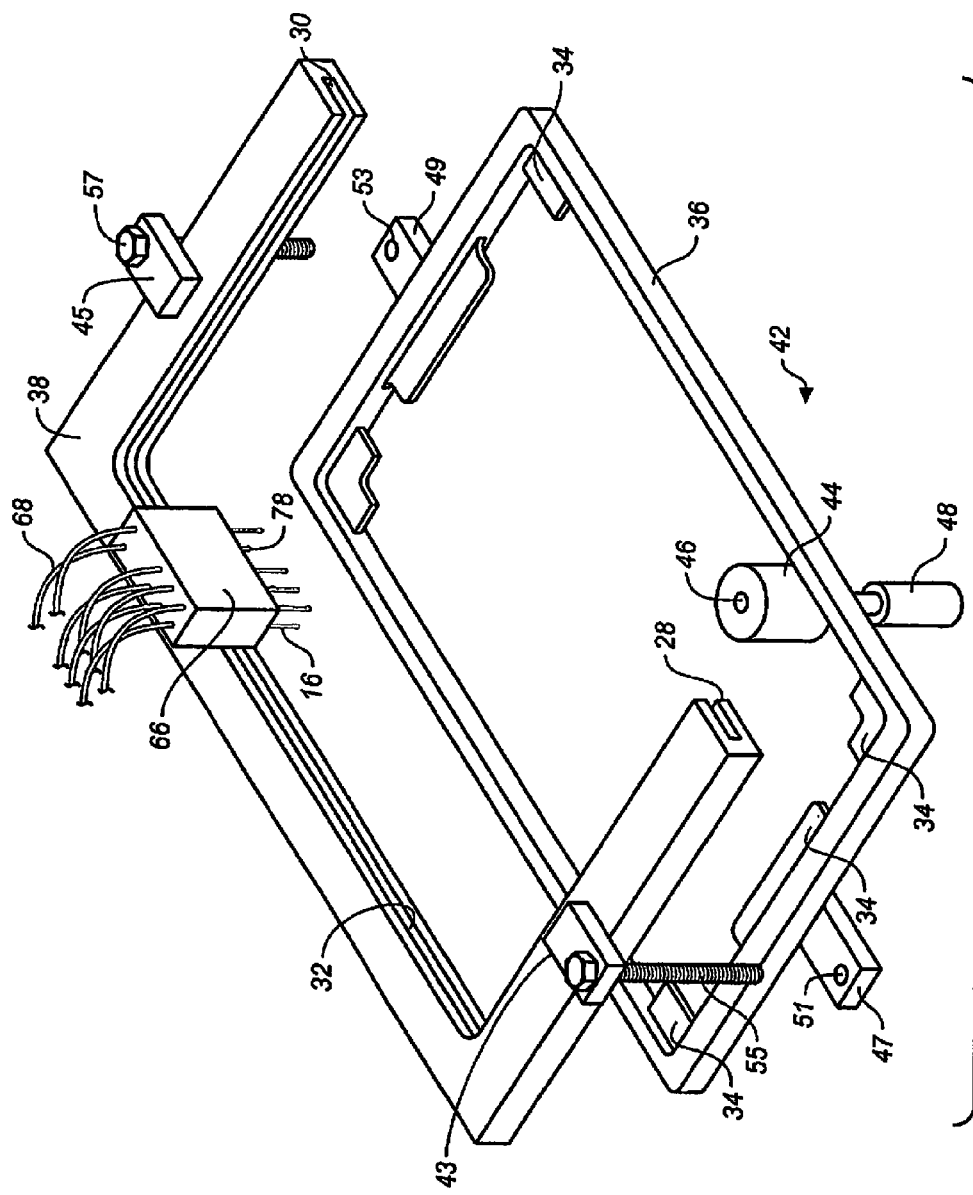
FIG._3

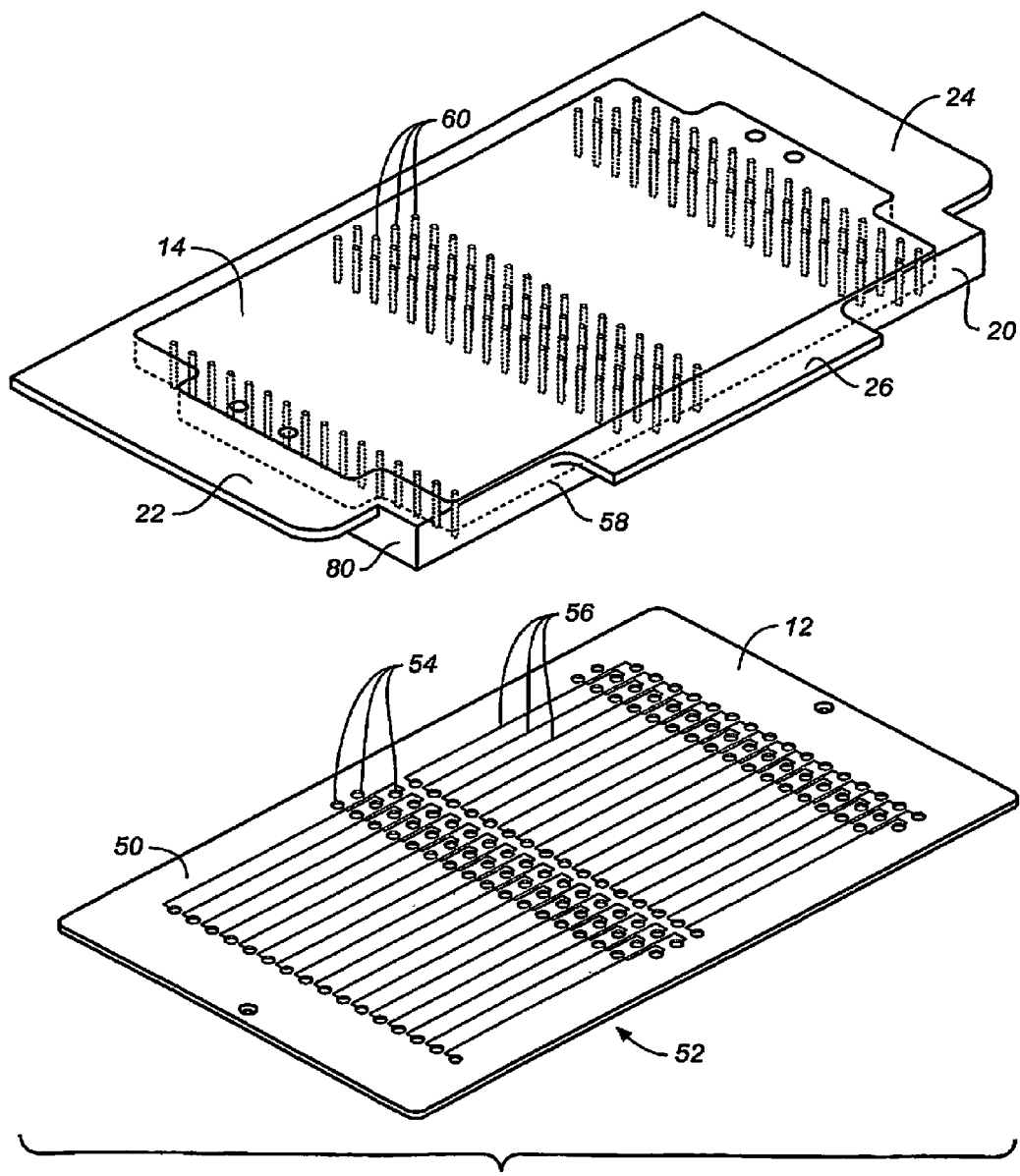
FIG._4

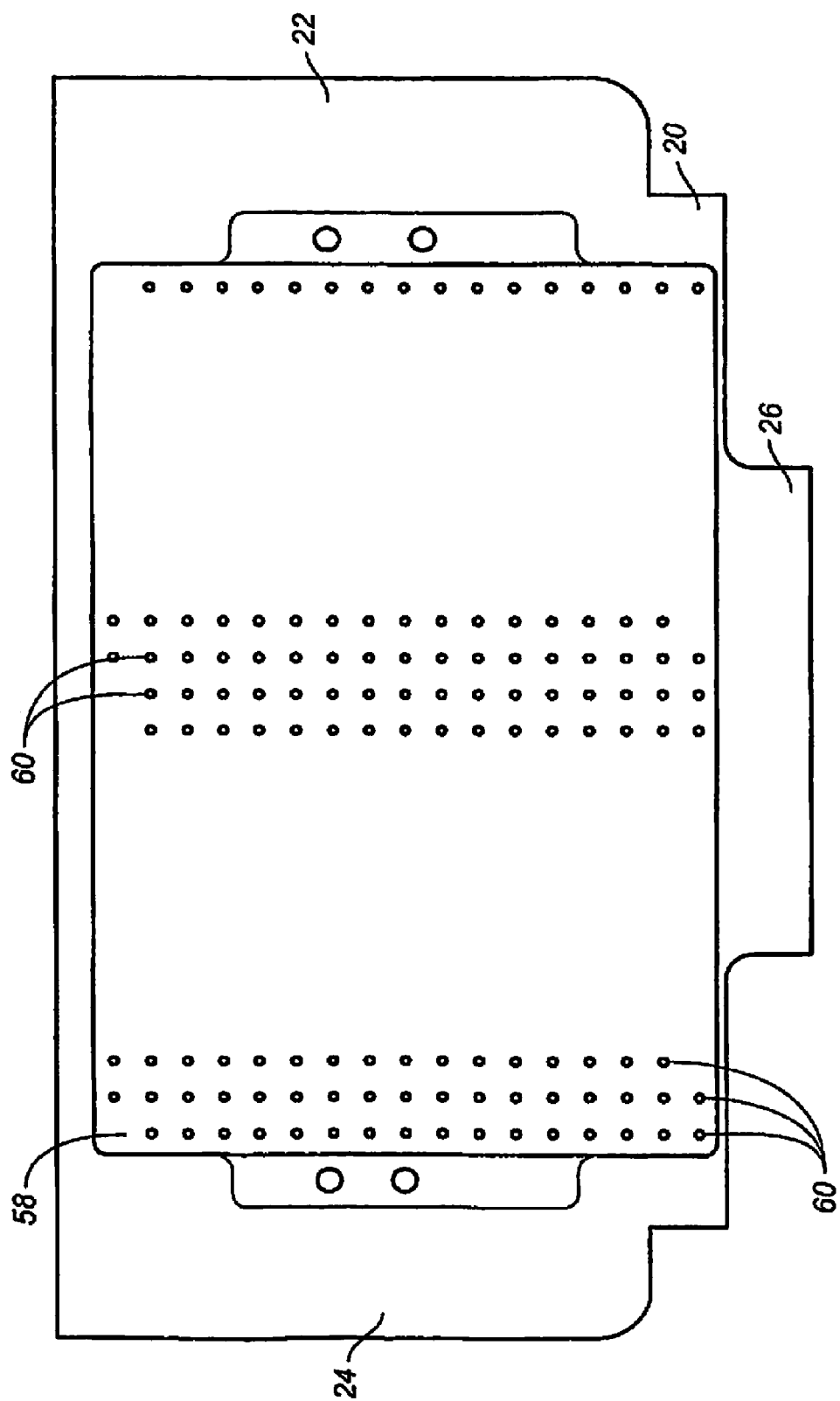
FIG._5

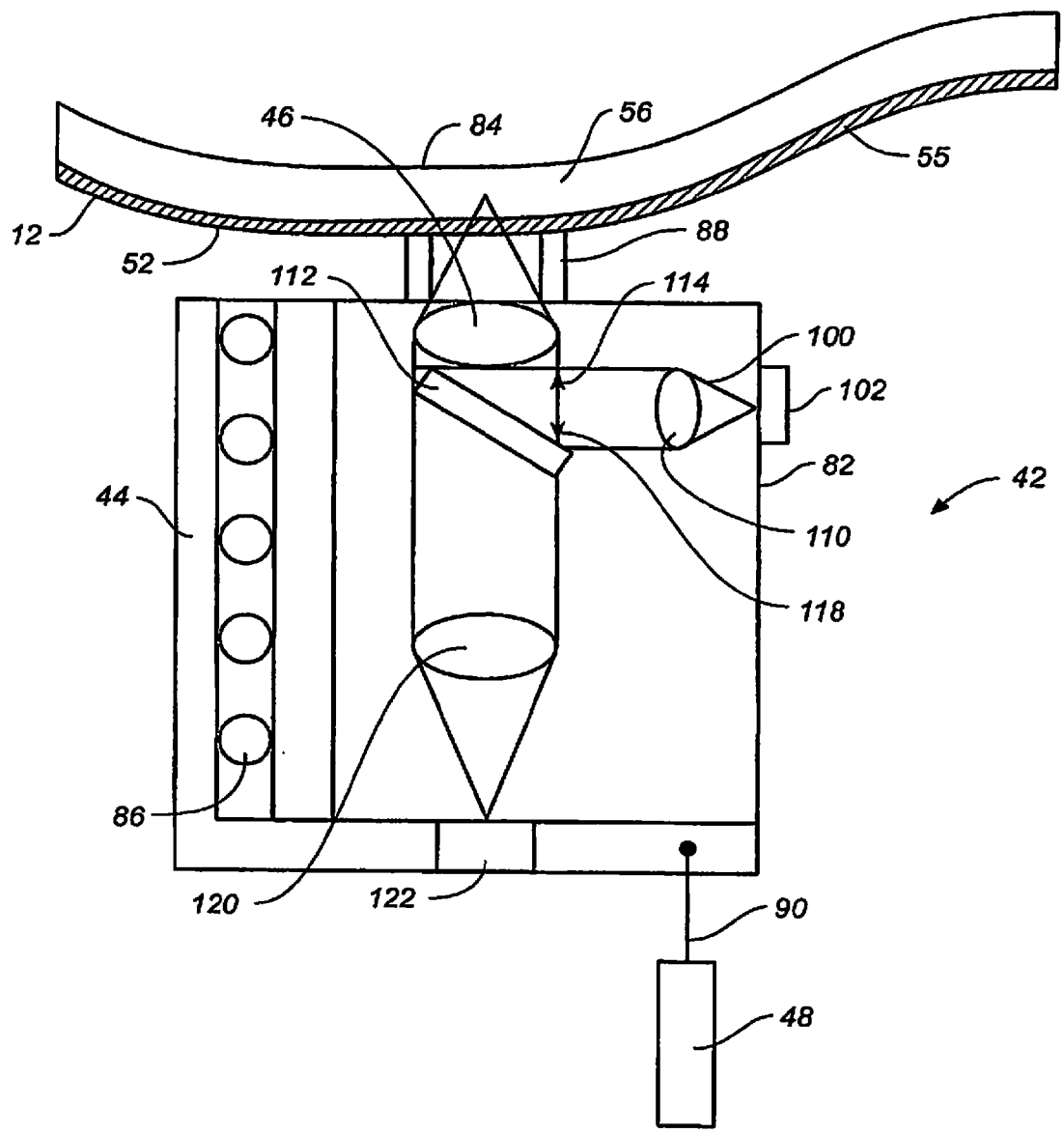
FIG._6

MICROFLUIDIC ANALYTICAL APPARATUS

This invention relates in general to microfluidic devices and analytical apparatus for using microfluidic devices to conduct chemical and biochemical sample analysis.

BACKGROUND OF THE INVENTION

Today's microfluidic chips are capable of reliably carrying out many chemical and reactions and analytical assays using minimal amounts reagents. These high throughput cards incorporate arrays of fluidic networks, each network having a multitude of ports or reservoirs and microchannels associated therewith. Examples of microfluidic chips, fluidic arrays, and their methods use are described in U.S. Pat. Nos. 5,750,015; 6,103,199 and published patent application Ser. No. 99/19717 assigned to the assignee and hereby incorporated by reference. In each network, reservoirs are provided for introduction of sample, reagents, test compounds, or liquid media. In some cases, microfluidic devices are manufactured with media already in the channels or reservoirs as appropriate.

Microfluidic chips have been used for separation and analysis of nucleic acids, proteins and other molecules. By utilizing electrokinetic methods such capillary electrophoresis (CE), dielectrophoresis, and isoelectric focusing, components of a sample can be resolved and analyzed. One method of species detection involves conventional laser induced fluorescence, also known as LIF. A variety of mechanisms known in the art can be used for this purpose. For example, fluorescent detection mechanisms can be used in conjunction with confocal microscopy. Publications such as U.S. Pat. No. 5,296,703 and PCT WO 98/49543 describe systems for detecting fluorescent signals in microchannel arrays.

Desirably, microfluidic chips can be manufactured from a variety of polymer materials leading to user convenience, disposability and affordability. These materials allow for standard manufacturing techniques including injection molding, compression molding, casting or hot embossing. One drawback however is that these methods all require heating and cooling of the chip substrate. Given variations between substrates in glass transition temperatures and varying exposure to both ambient and elevated temperatures, the resulting chips often include some level of warpage and/or minor defects. These irregularities can interfere with the intended operation of the chip. For example, detection systems may include robotics programmed to move to specific locations on a planar card. If the card is warped, these locations are difficult to reach or become inaccessible. Accordingly, it is desired to provide an accurate detection system that can compensate for inherent deficiencies in the microfluidic chip, such as warpage.

Another issue arises due to the fact that the intended application of a microfluidic chip generally dictates its design. For instance, longer CE separation channels are required for sequencing of long nucleic acid sequences while smaller and more concise CE networks can be used to conduct multiplexed enzyme assays. The result is that for different applications, the layout of fluidic network arrays from chip to chip will be different. Conventional analytical systems incorporate circuit (electrode) cards and voltage sources as fixtures. Accordingly, their versatility is limited, usually resulting in expensive systems dedicated to particular applications. For this reason, it is desired to have an analysis and detection system with the versatility to accommodate different chip designs in multiple configurations. Additionally, the chemical and biochemical reactions carried out in microfluidic chips are conducted using small quantities of sample and other fluids that easily evaporate. Therefore, a need also exists for a microfluidic analytical apparatus that alleviates evaporation of fluids within microfluidic chips.

SUMMARY OF THE INVENTION

The above mentioned objects are achieved with a microfluidic analytical apparatus featuring a microfluidic chip having a configuration of ports in connection with channels and a circuit card having a surface with an array of conductive pin groups aligning with and corresponding to the microfluidic ports, with pins terminating in conductive pads disposed on another surface of the circuit card, the conductive pads aligning and being in electrical communication with conductive fingers providing voltages.

In other words, the present invention pairs a microfluidic chip or card described above with a corresponding circuit card. The circuit card can be used repeatedly to provide voltages to microfluidic cards having the corresponding configuration in electrokinetic operations such as electrophoretic separation of analytes, the electrophoretic movement of molecules into or out of reaction chambers, isotachophoretic concentration of molecules, electroosmotic movement of fluidics through channels or chambers of the microfluidic card, or the like. The microfluidic card has a plurality of channels and ports on a top surface of the card, the ports in fluid communication with the channels. A multitude of configurations, including various numbers of channels and ports in various locations, are incorporated into different microfluidic cards. The circuit card has a plurality of conductive pins projecting from a bottom surface of the card and having a configuration that corresponds to a particular configuration of the ports of the microfluidic card with which it is paired.

The circuit card is received within a holder that provides multiple functions. In one embodiment, the holder acts as a stop, which results in the suspension of the pins within the corresponding ports when the circuit card is paired with the microfluidic card. Therefore, the conductive pins of the circuit card contact the fluid within the ports or electrical circuits within the card ports, but not the ports themselves. Additionally, when the conductive pins of the circuit card are received within the ports, the holder contacts the microfluidic card and provides a seal between the microfluidic card and the circuit card thus assisting in preventing evaporation of material within the ports.

An electrical connection between the microfluidic card and circuit card of the present invention is simple to form when the conductive pins, in electrical communication with a power source, are inserted within the corresponding ports. Conductive fingers connected to the power source provide voltages to the microfluidic card through the conductive pins of the circuit card. The pins of the circuit card are arranged in groups. The pins in each group are electrically connected through electrical traces to conductive pads that terminate on a top surface of the circuit card. The conductive pad configuration corresponds to the configuration of the conductive fingers. The conductive fingers contact the conductive pads and provide voltages to the pads, which travel to the traces and the conductive pins. When the conductive pins are received within the ports voltages are provided through the conductive fingers and various operations, including molecular separations of materials within the channels, can then take place.

During sample separation detection mechanisms known in the art are used for sample analysis. Detection is usually optical and usually the signal is generated by laser-induced fluorescence; the detector can be a confocal optical system known in the art. Other detection mechanisms, such as electrochemical detection, may also be employed In one embodiment of the invention, the detection mechanism such as a microscope is disposed within a holder that moves vertically during analysis in relation to the microfluidic card so as to maintain a constant distance from the surface of the microfluidic card. In one embodiment the microscope has a compliantly mounted head that is in sliding contact with the microfluidic card during analysis. The compliantly mounted head moves vertically in response to any non-uniformities or warpage that the card may have without requiring refocusing of the detection optics, since a constant distance from the optics to the card is maintained. This embodiment is particularly useful when microfluidic cards are made of plastic, or contain plastic components, such as covers, or the like, that although having well defined and precise small-scale structural features such as channel widths, wall thicknesses, port diameters, and the like, are susceptable to warpage, bends, and other defects, from manufacturing processes, handling, sample preparation, loading, or the like.

Support frames are provided for the circuit card and the microfluidic card. In one embodiment the support frames are adapted for movement of the cards in relation to the confocal microscope.

Apparatus according to the invention assist in providing multiple microfluidic manipulations at high throughput rates to allow for continuous processing of high number of analyses at high rates of speed. The complexity of mass screening programs is reduced for example by the simple to use configuration of the conductive fingers with respect to the conductive pads and the configuration of the conductive pins with respect to the microfluidic parts, thereby eliminating many of the manipulation steps that are required in the use of convention analytical apparatus.

BRIEF DESCRIPTION OF THE DRAWINGS

FIG. 1 is an exploded view of the apparatus of the present invention.

FIG. 2 is a perspective view of the apparatus of the present invention pictured in FIG. I in conjunction with support frames.

FIG. 3 is a perspective view of upper and lower frames of the apparatus of FIG. 2 supporting a microfluidic card and a circuit card.

FIG. 4 is an exploded view of the circuit card and the microfluidic card of the present invention pictured in FIG. 1.

FIG. 5 is a top view of a bottom surface of the circuit card of FIG. 4.

FIG. 6 is a plan view of the microfluidic card of FIG. 4 and of a detection mechanism

DETAILED DESCRIPTION OF THE INVENTION

With reference to FIGS. 1 and 2, there is seen an embodiment 10 of the present invention featuring a microfluidic card 12 paired with a circuit card 14 and conductive fingers 16 paired with conductive pads 18 of the circuit card 14. The conductive fingers 16 are electrically connected to and in electrical communication with a power source (not shown) and provide voltages to the circuit card 14 during analysis of sample within the microfluidic card 12. A detection system is employed for analysis of sample materials. In this embodiment of the invention, a microscope 42 is used as a part of the detection system; however, various detection systems known in the art may be used.

A holder 20 having wings 22, 24 and 26 holds the circuit card 14. Wing 26 can be used to grip the holder 20. The holder 20 is made from a rigid material such as for example, a rigid plastic.

With reference to FIGS. 2 and 3 it is seen that wings 22 and 24 of circuit card 14 slide within partially enclosed channels 28 and 30, respectively of an upper support frame 38 and a distal end 25 slides within partially enclosed channel 32 of the upper frame. Grip 26 is proximal to the user and can be used to insert the holder within the channels.

Shelves 34 upon which the microfluidic card 12 rests are also seen. The shelves 34 are a part of a lower support frame 36. Other ways of maintaining the microfluidic card in place include clips, channels, grooves, adhesives, vacuums and differential pressure.

When a downward force is applied to the upper frame 38 the holder 20 and the circuit card 14 held by the holder move in a downward direction so that the circuit card 14 makes contact with and pairs with microfluidic card 12 as seen in FIG. 2 and as described with reference to FIG. 4 below. A securing device such as a pair of clamps 40 and 41, attached to the frames 36 and 38, maintains the downward position of the upper frame 38 and thus the circuit card holder 20. Each clamp includes for example, upper plates 43 and 45 having apertures (not shown) attached to the upper frame 38, lower plates 47 and 49 having apertures 51 and 53, and fasteners 55 and 57 insertable through the apertures to clamp upper frame 38 down upon lower frame 36. When the clamps 40 are released (for example the fastener is removed from the apertures) the upper frame 38 is moved back to an upward position away from lower frame 36 as seen in FIG. 3. Alternatively, pneumatic, electromagnetic or electromechanical securing mechanisms, as well as other mechanisms known in the art, may be used in addition to or in replacement of clamps 40.

Positioned beneath the lower frame 36 is the microscope 42 disposed within a holder 44 adjacent to the microfluidic card 12 (when card 12 rests upon shelves 34) used for detecting migrated samples within the card 12. The microscope includes a lens 46, which is facing the microfluidic chip 12. The microscope holder 44 is attached to an air cylinder 48, which provides vertical movement to the microscope 42 through the holder 44. In one embodiment additional actuators provide lateral movement Other mechanisms for providing responsive vertical movement of the microscope optical head or lens known in the art may be used, such as springs or similar mechanical devices, electromagnetic suspension of the type used in optical readers of compact disc players, and the like.

With reference to FIG. 4 there is seen the microfluidic card 12 used in conjunction with the present invention having an upper first opposed major surface 50 and a lower second opposed major surface 52. The card 12 may include various configurations of ports 54 on the surface 50 and channels 56 within surfaces 50 and 52 and is not limited to the configuration shown here. The configuration of channels and ports are within a solid substrate making up the card, which may be an inflexible substrate or a flexible substrate, such as a film. If the card is flexible, it will usually be supported and oriented in conjunction with a rigid support. In the present example, the card 12 being used is non-flexible, therefore it is not used in conjunction with a rigid support. A portion of the microchannels 56 is used as a detection site, to detect migrated samples. The channels comprising the detection site will generally have a depth of about 10 to 200 µm and a width ranging from about 1 to 500 µL The channels may be parallel or in various arrays and configurations. Depending on the purpose of the chip and the pattern of the channels, whether the channels are straight, curved or tortuous, the chip may only be 1 or 2 cm long or 50 cm long, generally being from about 2 to 20 cm long. The width will vary with the number and pattern of channels, generally being at least about 1 cm, more usually at least about 2 cm and may be 50 cm wide. The chip has ports, usually reservoirs for materials such as sample, buffer and waste that are connected to the channels. Additional channels may be connected to the main channel for transferring samples and reagents, etc. to the main channel.

The circuit card 14 has upper and lower opposed major surfaces. With reference to FIGS. 4 and 5 a lower second opposed major surface 58 of the circuit card 14 will now be described. A phantom view of the lower second opposed major surface 58 of the circuit card 14 is seen in FIG. 4 and a top plan view of the second opposed major surface 58 is seen in FIG. 5. FIGS. 4 and 5 show an array of conductive pins 60 protruding from the second major surface 58. The pins 60 have a configuration that corresponds to a particular configuration of the ports 54 of the particular microfluidic card 12 that it is paired with. For instance, in this example the array of pins 60 has the same configuration as the ports 54 pictured on the microfluidic card 12 (FIG. 4) and the number of pins 60 is equal to the number of ports 54. The conductive pins 60 are fine wires used as electrodes mounted on the underside 58 of circuit card 14. The wires are usually platinum or other material with good electrical conductivity, substantially nonreactive (for example, platinum and gold) and corrosion resistant having a diameter of for example, 200 to 500 micrometers. The pins may be rigid or compliant For example, they may be spring-loaded or accordion-like. The electrode pins 60 act as cathodes and anodes for the separation of sample within the channels 50 and provide other voltages to the microfluidic card 12 for various operations. Electrode pins 60 may form wet or dry contacts with microfluidic card 12.

With reference to FIGS. 1 and 2 the upper surface of circuit card 14 is seen. First opposed major surface 62 of circuit card 14 has a plurality of conductive traces 64 that are connected to the array of conductive pins 60 on the second major surface 58. Traces 64 terminate in conductive pads 18 on the top surface 62 electrically connected to conductive pins 60.

The conductive pins 60 are arranged in groups of pins on the second major opposed surface 58 wherein a particular group of pins is electrically connected to the same conductive pad 18 through traces 64. Traces 64 may be present on either the first or second opposed major surfaces 58 and 62, on both of the surfaces, (as indicated in FIG. 2), or in between the surfaces. The conductive pads 18 are electrically connected to an electrical power source (not shown) through conductive fingers 16 (FIG. 1). The power source is provided with controls to change the voltages at the conductive fingers 16 thus at the conductive pads 18 in physical contact with the fingers 16 and to the conductive pins 60 in electrical contact with the pads 18. The voltages are provided in a pattern determined according to the sequence of electroflow manipulations to be carried out in the microfluidic card during analysis. Conductive fingers 16 are made from any material with good electrical conductivity. Conductive fingers 16 extend from apertures (not shown) within block 66 and are connected to a power source at one end through electrical wiring 68 extending from block 66. Wiring 68 provides voltages to the conductive fingers 16.

The conductive fingers 16 are arranged in a configuration that corresponds to the configuration of conductive pads 18 found on the first major surface 62 of circuit card 14. In FIGS. 1-3 eight conductive fingers 16 are seen arranged in columns 70 of two fingers 16. Three of the columns 70 are grouped together and a space 78 separates them from a fourth column.

Conductive pads 18 on circuit card 14 are arranged in the same configuration as the conductive fingers 16. Specifically, the pads 18 are arranged in groups of three columns close together and a fourth column spaced apart. In the example pictured there are more conductive pads 18 than conductive fingers 16. However, in another embodiment the same number of conductive pads as conductive fingers is present. Arranging the conductive pads 18 in the same configuration as the conductive fingers 16 provides that an electrical connection between conductive pads 18 and conductive fingers 7 . . . 6 is easily established as the conductive fingers 16 pair with the conductive pads 18. The conductive fingers 16 move horizontally along the top surface 62 of the circuit card 14 and move vertically to align and make contact with conductive pads 18. As the conductive fingers are moved along to make contact with pads 18 various groupings of pads 18 are provided with voltages. These voltages are provided to pins 60 and ports 54 of the microfluidic card 12 so that sample analysis may occur.

With reference to FIGS. 2-3, lower frame 36 and upper frame 38, in one embodiment, can move in a lateral or vertical position along tracks (not shown) to properly position the microfluidic card 12 and circuit card 14 for analysis by the microscope 42.

Referring back to FIG. 4, the conductive pins 60 are removably insertable within the ports 54 of the microfluidic chip 12. As stated above with regard to FIGS. 2 and 3 clamps 40 and 41, attached to the frames 36 and 38, maintain the downward position of the upper frame 38 supporting the circuit card holder 20. The holder 20 rests against card 12 and the conductive pins 60 enter and are suspended within the ports 54. In one embodiment, edges 80 of the holder 20 act as stops that prevent the conductive pins 60 from contacting a bottom surface of ports 54.

Additionally, the clamps 40 and 41 press the holder 20 against the card 12 forming a seal over the card. Fluids are sealed in the ports 54 and channels 56 when this seal is formed inhibiting evaporation of the fluids contained within the ports and channels.

There are many possible configurations and numbers of ports 54 and channels 56 that can be present on microfluidic cards 12 and corresponding configurations and numbers of the conductive pins 60 that are present on the circuit card 14 dependent on the type of desired analysis. By manufacturing a circuit card 14 that has conductive pads 18 that are configured as the conductive fingers 16 are, it is easy to establish electrical connections to the conductive pads 18 and to the electrically connected conductive pins 60 thus providing voltages to the ports 54 and channels 56 of the microfluidic device 12 for a desired operation. Regardless of the configuration of ports 54 and channels 56 and corresponding conductive pins 60, the configuration of the conductive pads 18 remains constant. The conductive pads 18 are configured to correspond to the arrangement of the conductive fingers 16. Therefore, the conductive finger 16 configuration will not have to be altered before analysis takes place, increasing the efficiency of the analysis. Additionally, various types of microfluidic cards 12 and corresponding circuit cards 14 can be produced, and yet each card 12, regardless of the configuration, can be easily interchangeable for use with the apparatus 10.

When the conductive pins 60 are suspended within the ports 54 and are connected to the appropriate voltage sources through conductive pads 18 and conductive fingers 16, samples from the ports 54 can be moved from the ports into the separation channels 56 using an electric field. The separation channels are loaded with an appropriate separation medium The voltages are changed to then separate the samples by means of electrophoresis. During sample separation a detection region on the microfluidic card 12 is scanned using microscope 42 pictured in FIG. 1.

With reference to FIG. 6, it is seen that in one embodiment of the present invention, the microscope 42 has a compliantly mounted optical head 82 within holder 44. The head 82 includes at least one of the optical elements described below. The compliant mounting mechanism used to mount the head 82 can be any mechanism that provides a vertical movement to the head that is responsive to deformities, such as warpage, or other irregularities, in the surface of microfluidic card 12. Preferably, the head is rigidly mounted in every direction except the vertical direction, i.e. the head is rigidly mounted in directions parallel to the surface of microfluidic card 12. "Rigidly mounted" means that the xy-position above (or below) the surface of microfluidic card 12 is controlled by a user, e.g. through conventional position controller under computer program control, or the like. A wide variety of methods may be used to provide a compliant mounting for the lens that allows the lens to move vertically relative to the surface of the microfluidic card in response to deformities. Such methods include using a spacer mounted with the lens together with a forcing means for applying a force perpendicular to the surface of the microfluidic card onto the lens so that the spacer is held in slidable contact with the surface of the microfluidic card. Preferably, the spacer is a cylindrical spacer coaxially mounted with the lens so that optical signals' emanating from a channel in the microfluidic card can be collected by the lens. Forcing means include springs, electromagnetic force, hydraulic force, such as compressed air, elastomeric materials, or the like. The head may move vertically through the use of, for example, air cylinder 48. Air cylinder 48 is connected through a mechanical connection, for example, push rod 90 to head 82. The air cylinder 48 provides vertical movement of the holder 44 along surfaces of the microfluidic card 12 including deformities 84. Deformities 84 include non-planar or warped surfaces. Roller bearings 86 rigidly mount the head 82 in the lateral direction and prevent the head from pivoting with the holder 44. The air cylinder 48 moderates the force that is applied to the head 82. The air cylinder is, for example, a soft air cylinder providing for example, 1-2 pounds of force that pushes a piston (not shown) of the cylinder upwardly and downwardly in a spring-like manner. Therefore, the moderate force that the air cylinder 48 provides helps to prevent damage to the microscope head 82 and to the card 12 when the head 82 is moved vertically by the air cylinder 48 to contact the card 12. As the head 82 is compliantly mounted it is able to move within the holder and to make contact with the card 12. In one example, nose piece 88 of the head 82 is able to travel along in a sliding contact relation with a surface of the microfluidic card 12, such as second opposed major surface 52 even when the card has deformities 84, without damaging the head 82. Nose piece 88 rests against the surface 52 of the card 12 and in conjunction with the air cylinder 48 and compliant mechanism allowing for vertical movement maintain lens 46 at the correct distance from the channels within the card. Therefore, a significant attribute of the microscope 42 is that it is able to track the samples within channels 56 through wall 55 even though the channels and sample may be located within a card having non-uniform surfaces, without requiring refocusing of detection optics. Samples within channels 56 that otherwise could not be detected without manipulation of the detection optics or accurately detected with prior art mechanisms relying on a uniform shape of card can now be detected with ease.

In another embodiment, optical head 82 of microscope 42 may be rigidly mounted with collar, or nose piece, 88 and lens 46 compliantly mounted within optical head 82 so that they are responsive to deformities, warpage, or other irregularities in the surface of microfluidic card 12.

Optical elements within head 82 are elements known in the art used for sample detection. For example, these elements include an illumination beam 100 from illumination source 102 that passes through a lens 110, which serves to collect divergent light The beam 100 is then reflected by dichroic mirror 112, which reflects light of the excitation wavelength of interest to pass through the mirror. The reflected beam 114 is focused by lens 46 and forms a small sharp beam, which passes into the detection regions of channels 56. Fluorophores within the channel will be excited and will emit light, which will exit the channel and be collected by lens 46. The emitted beam 118 will pass through dichroic mirror 112 and through lens 120 which focuses light beam 118 on photodetector 122. The photodetector converts this light to electric signals for processing. The method by which the microscope 42 uses the excitation beam to scan the microfluidic card 12 can be a conventional confocal optical system known in the art or other detection mechanisms known in the art may be employed. The arrangement of optical elements described above may be substituted with other arrangements and types of optical elements used for sample detection.

The invention claimed is:

1. A microfluidic analytical apparatus comprising:
  a microfluidic card having,
    (a) first and second opposed major surfaces,
    (b) a plurality of microchannels formed between the major surfaces, each microchannel having ports extending to the first major surface of the microfluidic card, thereby forming an array of ports,
  a circuit card in moveable proximity to the microfluidic card having,
    (i) first and second opposed major surfaces,
    (ii) an array of conductive pins projecting from said second surface and disposed adjacent to and projecting toward the first major surface of said microfluidic card in a removably receivable relation with selected ports thereof, said array of pins corresponding to a select array of ports and said pins being arranged in groups,
    (iii) conductive pads disposed on said first surface of said circuit card, each pad corresponding to and electronically connected to a group of pins, and
  conductive fingers in electrical communication with a power source and making electrical contact with said pads, said fingers movable horizontally along the first surface of the circuit card, thereby aligning with said pads.

2. The apparatus of claim 1 further comprising a circuit card holder.

3. The apparatus of claim 2 wherein said holder includes a stop and said stop prevents said conductive pin from contacting a port surface when received by said port.

4. The apparatus of claim 1 further comprising:
  an optical head disposed in a holder adjacent to, and in sliding contact relation with, the second major surface of the microfluidic card.

5. The apparatus of claim 4 wherein said optical head includes a nose protruding from said head and said nose is in a sliding contact relation with the second major surface of said card.

6. The apparatus of claim 4 further comprising roller bearings wherein said bearings rigidly mount said head in a lateral direction relative to the second major surface of the microfluidic card within said holder.

7. The apparatus of claim 6 further comprising an air cylinder providing vertical movement to said head.

8. The apparatus of claim 1, wherein the plurality of microchannels comprise an array of parallel channels.

9. The apparatus of claim 8, wherein the parallel channels are arranged in groups.

10. A microfluidic analytical apparatus comprising:
a microfluidic card having first and second opposed major surfaces, a plurality of microchannels formed between the major surfaces, each microchannel having ports extending to the first major surface of the microfluidic card, thereby forming an array of ports;
a circuit card in moveable proximity to the microfluidic card, the circuit card having first and second opposed major surfaces, an array of conductive pins projecting from said second major surface of the circuit card and disposed adjacent to and projecting toward the first major surface of the microfluidic card in a removably receivable relation with selected ports thereof, and conductive pads disposed on the first major surface of the circuit card, the pads corresponding to and electronically connected to the array of pins; and
conductive fingers in electrical communication with a power source, the fingers movable horizontally along the first surface of the circuit card, the fingers thereby aligning with and making electrical contact with the pads; and
a circuit card holder,
wherein said circuit card is disposed within said holder and said holder rests against said microfluidic card when said card receives said conductive pins, thereby forming a seal between said circuit card and said microfluidic card.

11. The apparatus of claim 10 wherein said circuit cardholder includes a stop and said stop suspends said conductive pins within said ports.

12. A microfluidic analytical apparatus comprising:
a circuit card for use with a microfluidic card having a plurality of ports and channels connecting the ports, and a power supply, providing electrical contact with one or more ports in a microfluidic chip, said circuit card comprising:
first and second opposed major surfaces,
one or more conductive pads disposed on said first surface, adapted for electrical connection to the power supply, and
a plurality of conductive pins projecting from said second surface, said pins being in electrical communication with said one or more conductive pads and adapted to be inserted directly within the ports of the microfluidic card for supplying an electrical field to the ports, to effect an electrokinetic process within the microfluidic card channels;
conductive fingers in electrical communication with the power supply, the fingers movable horizontally along the first surface of the circuit card, the fingers thereby aligning with and making electrical contact with the one or more pads; and
an optical head compliantly disposed in a holder, said head adjacent to the second major surface of the microfluidic card and in sliding contact relation with the second opposed major surface of the microfluidic card.

13. The microfluidic analytical apparatus of claim 12 further comprising:
a microfluidic card, wherein said microfluidic card includes a non-uniform surface and said compliantly mounted optical head is in a sliding contact relation with said non-uniform surface.

14. The microfluidic analytical apparatus of claim 12, further comprising a circuit card holder.

\* \* \* \* \*